United States Patent
Lesso

(10) Patent No.: US 11,534,100 B2
(45) Date of Patent: Dec. 27, 2022

(54) ON-EAR DETECTION

(71) Applicant: Cirrus Logic International Semiconductor Ltd., Edinburgh (GB)

(72) Inventor: John P. Lesso, Edinburgh (GB)

(73) Assignee: Cirrus Logic, Inc., Austin, TX (US)

( * ) Notice: Subject to any disclaimer, the term of this patent is extended or adjusted under 35 U.S.C. 154(b) by 0 days.

(21) Appl. No.: 17/094,867

(22) Filed: Nov. 11, 2020

(65) Prior Publication Data

US 2021/0186350 A1 Jun. 24, 2021

Related U.S. Application Data

(60) Provisional application No. 62/949,630, filed on Dec. 18, 2019.

(51) Int. Cl.
*A61B 5/00* (2006.01)
*A61B 5/349* (2021.01)

(52) U.S. Cl.
CPC ............ *A61B 5/349* (2021.01); *A61B 5/4803* (2013.01); *A61B 5/6817* (2013.01); *A61B 5/725* (2013.01); *A61B 2562/0219* (2013.01)

(58) Field of Classification Search
CPC ..... A61B 5/6803; A61B 5/0006; A61B 5/318; A61B 5/6815; A61B 7/04; A61B 5/02; A61B 5/6816; A61B 7/00; A61B 5/28; A61N 1/36031; A61N 1/36014; A61N 1/36036

See application file for complete search history.

(56) References Cited

U.S. PATENT DOCUMENTS

| | | | | |
|---|---|---|---|---|
| 7,914,468 B2 * | 3/2011 | Shalon | ................. | A61B 5/4205 600/590 |
| 8,705,784 B2 * | 4/2014 | Haartsen | ................ | H04R 29/00 381/328 |
| 2010/0189268 A1 | 7/2010 | Haartsen et al. | | |
| 2018/0227755 A1 | 8/2018 | Abernathy et al. | | |
| 2019/0294769 A1 | 9/2019 | Lesso | | |

OTHER PUBLICATIONS

International Search Report and Written Opinion of the International Searching Authority, International Application No. PCT/GB2020/052788, dated Mar. 30, 2021.
Beritelli, Francesco et al: "Biometric Identification Based on Frequency Analysis of Cardiac Sounds", IEEE Transactions on Information Forensics and Security, IEEE, Piscatway, NJ, US, vol. 2, No. 3, Sep. 1, 2007.
Eberhard Sengpiel: "Prinzip der elektro-akustischen Wandlung", Jun. 1, 2002, Retrieved from the Internet: http://www.sengpielaudio.com/PrinzipDerElektro-AkustischenWandlung.pdf (retrieved Jun. 21, 2016), no translation available.

* cited by examiner

*Primary Examiner* — Deborah L Malamud
(74) *Attorney, Agent, or Firm* — Jackson Walker L.L.P.

(57) ABSTRACT

A sensor on an earpiece is used to attempt to detect a signal corresponding to a heartbeat. If a heartbeat is detected, it can be determined that the earpiece is being worn by a user. The sensor may be an acoustic transducer on a surface of the earpiece that is located within the wearer's ear canal, while the earpiece is being worn normally.

28 Claims, 6 Drawing Sheets

ON-EAR DETECTION

The present disclosure claims priority to U.S. Provisional Patent Application Ser. No. 62/949,630, filed Dec. 18, 2019, which is incorporated by reference herein in its entirety.

TECHNICAL FIELD

This relates to an earphone system, and in particular to a system that allows for detection of when an earphone is within a user's ear.

BACKGROUND

Many electronic devices include earphones, and it is known to be advantageous to detect when the earphones are being worn, that is, when the earphones are on or in the ears of a user. When it is determined that an earphone is not being worn, steps can be taken to reduce power consumption, for example by suspending playback of audio signals through the earphone or powering down an output amplifier connected to a loudspeaker of the earphone.

Many systems for on-ear detection require additional components to be provided in the earphone, thereby adding to the cost and complexity of the device.

As another example, an acoustic on-ear detector may be provided in an earphone that includes two microphones, with one of the microphones facing into the user's ear canal when the earphone is being worn normally, and the other microphone facing outwardly for detecting ambient sounds. This system compares the sounds detected by the two microphones. However, this means that, when the user is not speaking, or when the earphone is not being used to play sounds that the user is listening to, the on-ear detection still requires sounds (typically infrasonic or ultrasonic tones that will not be heard by the user) to be played through the loudspeaker of the earphone. This in turn requires the loudspeaker driver amplifier to be powered up, and this has a significant power consumption.

SUMMARY

According to a first aspect of the present invention, there is provided a method of detecting whether an earpiece is being worn by a user, the method comprising:
using at least one sensor on the earpiece to detect a heartbeat; and
if a heartbeat is detected, determining that the earpiece is being worn by a user.
The method may further comprise:
if no heartbeat is detected, determining that the earpiece is not being worn by a user; and
determining that a speech signal detected by a microphone on the earpiece may not come from a live speaker.
The method may further comprise:
if no heartbeat is detected, determining that the earpiece is not being worn by a user; and
powering down an output amplifier connected to a loudspeaker of the earpiece.
The method may further comprise:
if no heartbeat is detected, determining that the earpiece is not being worn by a user; and
suspending playback of audio signals through the earpiece.

The step of using at least one sensor on the earpiece to detect a heartbeat may comprise using an accelerometer on the earpiece to detect vibrations indicative of a heartbeat.

The step of using at least one sensor on the earpiece to detect a heartbeat may comprise using a contact microphone on the earpiece to detect vibrations indicative of a heartbeat.

The step of using at least one sensor on the earpiece to detect a heartbeat may comprise detecting electrical signals associated with a heartbeat.

The step of using at least one sensor on the earpiece to detect a heartbeat may comprise using an optical sensor to obtain a photoplethysmogram.

The step of using at least one sensor on the earpiece to detect a heartbeat may comprise using an inertial measurement unit configured to detect movement in an ear canal of the user if the earpiece is being worn by the user.

The step of using at least one sensor on the earpiece to detect a heartbeat may comprise using at least one audio transducer to obtain a signal representing sound in the vicinity of the earpiece. The at least one audio transducer may comprise a microphone on the earpiece, or may comprise a loudspeaker on the earpiece.

The method may further comprise:
applying said signal representing sound in the vicinity of the earpiece to an analog-digital converter, wherein the analog-digital converter is switched on only when detecting whether the earpiece is being worn by a user.
The method may comprise:
using a first audio transducer to generate a first audio signal, wherein the first audio transducer is positioned on the earpiece so as to detect sounds in an ear canal of a user, when the earpiece is being worn normally;
using a second audio transducer to generate a second audio signal, wherein the second audio transducer is positioned on the earpiece so as to detect sounds outside an ear of a user, when the earpiece is being worn normally;
applying the second audio signal to an adaptive filter to generate a filtered second audio signal, wherein the adaptive filter is configured to represent a transfer function experienced by sound travelling from outside the ear of a user to inside the ear canal of the user; and
subtracting the filtered second audio signal from the first audio signal to generate said signal representing sound in the vicinity of the earpiece.
The method may further comprise:
applying the signal representing sound in the vicinity of the earpiece to a first input of a subtractor;
applying a signal to be applied to a loudspeaker in the earpiece to an adaptive filter to generate a filtered signal; and
applying the filtered signal to a second input of the subtractor,
wherein the adaptive filter is adapted to reproduce an effect of applying the signal to the loudspeaker and detecting the resulting sound using said at least one audio transducer, such that an effect of the signal to be applied to the loudspeaker is minimised in an output of the subtractor.

The step of using at least one sensor on the earpiece to detect a heartbeat may comprise:
receiving a signal from the sensor;
obtaining samples of the received signal;
calculating an autocorrelation using the samples of the received signal;
detecting the heartbeat from at least one peak in the calculated autocorrelation.

The method may comprise obtaining said samples of the received signal at a sample rate below 1 kHz.

The method may comprise receiving the signal in digital form with a sample rate higher than 1 kHz, and downsampling the received signal to a sample rate below 1 kHz.

The step of detecting the heartbeat from at least one peak in the calculated autocorrelation may comprises:
ignoring peaks that correspond to frequencies below a range of likely human heart rates; and
ignoring peaks having a height below a threshold height.

The step of using at least one sensor on the earpiece to detect a heartbeat may comprise:
receiving a signal from the sensor; and
determining whether said signal contains a component at a frequency consistent with a heartbeat, for example in the region of 0.75 Hz-3 Hz.

Determining whether said signal contains a component at a frequency consistent with a heartbeat may comprise:
band-pass filtering the signal to pass components of the signal in a frequency range consistent with a heartbeat, and
detecting a peak component of the band-pass filtered signal.

Determining whether said signal contains a component at a frequency consistent with a heartbeat may comprise:
applying said signal to a Kalman Filter.

Determining whether said signal contains a component at a frequency consistent with a heartbeat may comprise:
applying said signal to a phase locked loop, and determining a frequency at which the loop is locked.

The step of using at least one sensor on the earpiece to detect a heartbeat may comprise:
receiving a signal from the sensor; and
applying said signal to a neural network that has been trained to recognise signals representing heartbeats.

The method may comprise:
using at least one first sensor on the earpiece to detect a heartbeat; and
if a heartbeat is detected, making a preliminary determination that the earpiece is being worn by a user, and activating at least one second sensor on the earpiece;
using the at least one second sensor on the earpiece to detect a heartbeat; and
if a heartbeat is detected, determining that the earpiece is being worn by a user.

The method may comprise:
receiving a first signal from at least one first sensor on the earpiece, wherein the at least one first sensor is positioned on the earpiece such that it is able to detect a heartbeat, when the earpiece is being worn in an expected way;
determining whether the first signal comprises features characteristic of a heartbeat;
receiving a second signal from at least one second sensor on the earpiece, wherein the at least one second sensor is positioned on the earpiece such that it is not able to detect a heartbeat, when the earpiece is being worn in the expected way;
determining whether the second signal comprises features characteristic of a heartbeat;
and
if it is determined that the first signal comprises features characteristic of a heartbeat and that the second signal comprises features characteristic of a heartbeat, determining that the earpiece is not being worn in the expected way; or
if it is determined that the first signal comprises features characteristic of a heartbeat and that the second signal does not comprise features characteristic of a heartbeat, determining that the earpiece is being worn in the expected way.

According to another aspect of the present invention, there is provided a system configured for performing a method according to the first aspect.

According to another aspect of the present invention, there is provided a system comprising a processor, wherein the processor is configured for performing a method according to the first aspect.

According to another aspect of the present invention, there is provided a computer program product, comprising a tangible and/or non-volatile computer readable medium, comprising computer readable instructions for causing a processor to perform a method according to the first aspect and the second aspect.

According to a second aspect of the present invention, there is provided a method of biometric authentication, comprising:
using at least one sensor on an earpiece to detect a heartbeat of a person wearing the earpiece;
obtaining information about properties of the detected heartbeat; and
using the information about the properties of the detected heartbeat as a biometric identifier.

The step of using at least one sensor on the earpiece to detect a heartbeat may comprise:
using at least one audio transducer to obtain a signal representing a sound, the method further comprising obtaining information about properties of the detected heartbeat from the signal representing the sound.

The at least one audio transducer may comprise a loudspeaker on the earpiece.

Said properties of the detected heartbeat may comprise timing properties, and/or may comprise amplitude properties.

The step of using at least one sensor on the earpiece to detect a heartbeat may comprise:
receiving a signal from the sensor;
obtaining samples of the received signal;
calculating an autocorrelation using the samples of the received signal;
estimating a heart rate of the person wearing the earpiece from at least one peak in the calculated autocorrelation.

The method may comprise:
using at least one first sensor on the earpiece to detect a heartbeat; and
if a heartbeat is detected, making a preliminary determination that the earpiece is being worn by a user, and activating at least one second sensor on the earpiece; and
obtaining said information about properties of the detected heartbeat using the at least one second sensor.

According to a further aspect of the present invention, there is provided a system configured for performing a method according to the second aspect.

According to a further aspect of the present invention, there is provided a system comprising a processor, wherein the processor is configured for performing a method according to the second aspect.

According to a further aspect of the present invention, there is provided a computer program product, comprising a tangible and/or non-volatile computer readable medium, comprising computer readable instructions for causing a processor to perform a method according to the second aspect.

According to a third aspect of the present invention, there is provided a method of operation of an earphone, the method comprising:
  using at least one sensor on the earpiece to generate a sensor signal;
  using the sensor signal to detect a heartbeat; and
  if a heartbeat is detected, determining that the earpiece is being worn by a user; and
  determining a heart rate of the user;
  obtaining information about properties of the detected heartbeat; and
  using the information about the timing properties of the detected heartbeat as a biometric identifier of the user.

According to a further aspect of the present invention, there is provided a system configured for performing a method according to the third aspect.

According to a further aspect of the present invention, there is provided a system comprising a processor, wherein the processor is configured for performing a method according to the third aspect.

According to a further aspect of the present invention, there is provided a computer program product, comprising a tangible and/or non-volatile computer readable medium, comprising computer readable instructions for causing a processor to perform a method according to the third aspect.

According to a fourth aspect of the present invention, there is provided a method of detecting whether an earphone is being worn by a user, the method comprising, while playing sounds through a loudspeaker in the earphone:
  using at least one sensor on the earphone to detect a heartbeat; and
  if no heartbeat is detected, determining that the earphone is not being worn by a user, and pausing playing said sounds through said loudspeaker.

The method may further comprise:
  if no heartbeat is detected for a predetermined period of time, powering down a driver amplifier connected to supply signals to said loudspeaker.

According to a further aspect of the present invention, there is provided a system configured for performing a method according to the fourth aspect.

According to a further aspect of the present invention, there is provided a system comprising a processor, wherein the processor is configured for performing a method according to the fourth aspect.

According to a further aspect of the present invention, there is provided a computer program product, comprising a tangible and/or non-volatile computer readable medium, comprising computer readable instructions for causing a processor to perform a method according to the fourth aspect.

In some embodiments, this has the advantage that it can be determined whether an earpiece is being worn by a user, without requiring any additional components, or without generating any signals specifically for that purpose.

In some embodiments, this has the advantage that it provides an additional method of verifying the identity of a person wearing an earpiece.

BRIEF DESCRIPTION OF DRAWINGS

For a better understanding of the invention, and to show how it may be put into effect, reference will now be made, by way of example, to the accompanying drawings, in which.

DETAILED DESCRIPTION

The description below sets forth example embodiments according to this disclosure. Further example embodiments and implementations will be apparent to those having ordinary skill in the art. Further, those having ordinary skill in the art will recognize that various equivalent techniques may be applied in lieu of, or in conjunction with, the embodiments discussed below, and all such equivalents should be deemed as being encompassed by the present disclosure.

Figure 1:
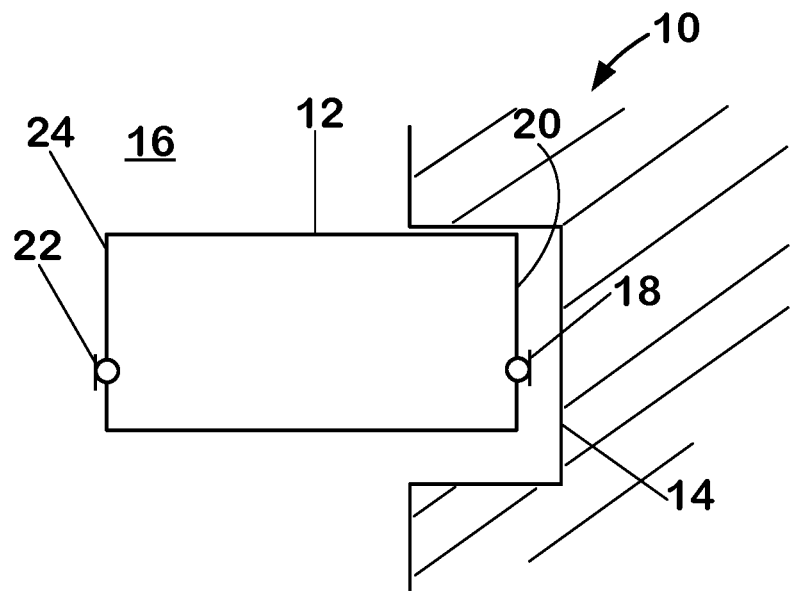
FIG. 1 illustrates an earbud in an ear.

FIG. 1 is a schematic illustration of an earbud in an ear. Specifically, FIG. 1 shows a part cross-sectional view through the head 10 of a person wearing an earbud, or in-ear type earphone, 12. A part of the earphone extends into the ear canal 14 of the wearer, while another part is exposed to the air 16.

Aspects of this disclosure relate to detecting whether the earphone is being worn, i.e. is in a person's ear, or whether it is not being worn. Specifically, it has now been recognised that this detection can be performed by detecting a heartbeat using at least one sensor on the earphone.

For example, the detection may comprise using an accelerometer on the earphone to detect vibrations, for example vibrations of the surface of the wearer's ear canal, that are indicative of a heartbeat.

As another example, the detection may comprise using an electrical contact to detect electrical signals in the internal surface of the wearer's ear canal, that are associated with a heartbeat.

As another example, the detection may comprise using an optical sensor on the earphone to obtain a photoplethysmogram that can be used to detect a heartbeat.

As another example, the detection may comprise using an inertial measurement unit configured to detect movement that would be expected in an ear canal of the user if the earphone is being worn.

In embodiments described in more detail below, using at least one sensor on the earphone to detect a heartbeat comprises using at least one audio transducer to obtain a signal representing sound in the vicinity of the earphone.

Thus, the heartbeat can be detected using acoustic means. Since the detection works by passively detecting the heartbeat, it is not necessary to power up a loudspeaker driver amplifier in the earphone, and hence power is saved when the device is not in the ear.

In the simplest case, a transducer that is located within the ear canal of a person wearing the earphone can be used to detect an acoustic signal, and sounds that result from blood flow in the wearer's head can be identified. These sounds result ultimately from the wearer's heartbeat, and so they have a component that depends on the wearer's heart rate. Thus, if the transducer detects an acoustic signal that is characteristic of a heartbeat, it can be assumed that the earphone is being worn by a person. A recording of the sounds made by a heart is referred to as a phonocardiogram.

Thus, in its simplest form, the method of on-ear detection can be performed with a single acoustic transducer.

In the embodiment shown in FIG. 1, the earphone 12 includes a first transducer 18 that is located on or within a surface 20 of the earphone that extends into the ear canal 14 of the wearer.

The transducer 18 may be a microphone. However, it has been recognised that many microphones have poor sensitivity at low frequencies. This is because many microphones are specifically designed to attenuate low frequencies (for example below 100 Hz), in order to improve their robustness to wind noise, and because package noise associated with a microphone typically increases at lower frequencies.

Because a heartbeat has a very low frequency, for example in the region of 1-2 Hz for most of the time, some embodiments use the loudspeaker, that is normally used for playing sounds into the ear of the wearer, as the transducer 18. Such a loudspeaker may have better sensitivity at these low frequencies than a typical microphone.

In the embodiment shown in FIG. 1, the earphone 12 also includes a second transducer 22 that is located on or within a surface 24 of the earphone that is exposed to the air 16. The transducer 22 may for example take the form of a microphone, that is provided on the earphone 12 for a purpose such as detecting the wearer's speech, or detecting ambient noise so that the noise can be cancelled by noise cancellation circuitry.

As described in more detail below, the use of a second transducer allows for the cancellation of sounds that are detected by the first transducer 18, but that result from ambient sounds rather than from sounds originating in the wearer's head.

Figure 2:
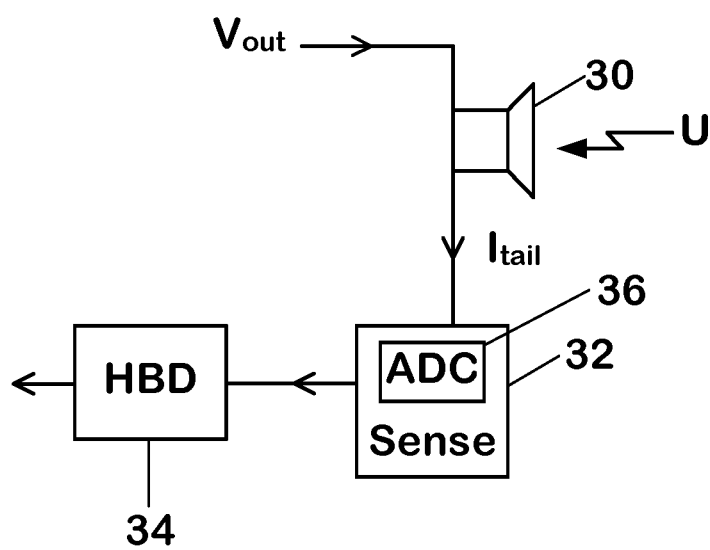
FIG. 2 illustrates a use of a loudspeaker as a microphone in an earbud as shown in FIG. 1.

FIG. 2 illustrates a use of a loudspeaker as a microphone in an earbud.

Specifically, FIG. 2 shows a loudspeaker 30, to which a signal $V_{out}$ is applied when it is desired to play sounds through the loudspeaker. In addition, the loudspeaker 30 responds to a pressure u that is incident on the diaphragm of the loudspeaker.

The result is that the current $I_{tail}$ on the output of the loudspeaker 30 depends not only on the signal $V_{out}$, but also on the pressure u, that results from the sounds originating in the wearer's head.

The current $I_{tail}$ is passed to a sensing block 32, and the output thereof is passed to a heartbeat detection (HBD) block 34.

The sensing block 32 may include a small, low bandwidth and low power consumption analog-digital converter (ADC) 36, for generating a digital signal corresponding to the current $I_{tail}$. In order to save power, the ADC 36 may be switched on only when it is desired to use the transducer 18 to detect the wearer's heartbeat.

The use of the loudspeaker 30 as the transducer for detecting the sounds, i.e. effectively as a microphone, means that the methods described herein can be used in earphones that do not have a dedicated microphone provided on an inward-facing surface of the earphone.

One issue that arises when detecting sounds to obtain a phonocardiogram in a person's ear canal is that external noise will leak into the ear canal and be detected by the acoustic transducer. This is attenuated to some extent when the person is wearing an earbud, but is particularly relevant for leaky earbuds, which do not provide an airtight seal between the wearer's ear canal and the outside.

Figure 3:
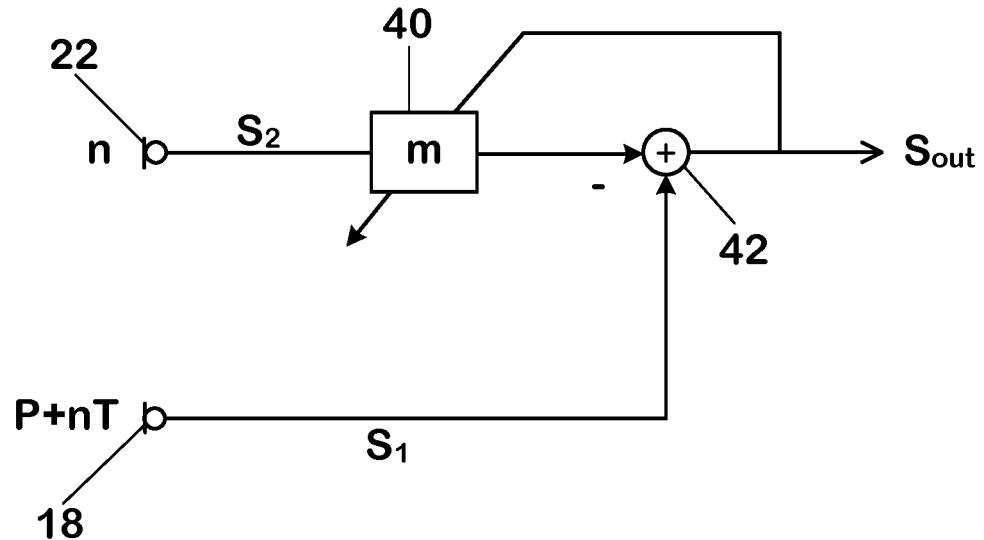
FIG. 3 illustrates a form of signal processing applied to a signal obtained from a microphone in an earbud as shown in FIG. 1.

FIG. 3 illustrates a form of signal processing applied to a signal obtained from a microphone in an earbud, in order to account for this external noise.

FIG. 3 shows an embodiment based on FIG. 1, in which there is a first transducer 18 inside the ear canal and a second transducer 22 on the outside of the earbud. The second transducer 22 detects external noise n, and this external noise is subject to a transfer function T of the sound leakage path and the associated acoustic coupling before being detected by the first transducer 18. The first transducer also detects the sounds P resulting from the wearer's heartbeat. Thus, the first transducer 18 generates a first signal $S_1$ that is dependent on (P+nT), and the second transducer 22 generates a second signal $S_2$ that is dependent on n.

The second signal $S_2$ is applied to an adaptive filter 40, with a transfer function m. The first signal $S_1$ is applied to a first input of a subtractor 42, and the output of the adaptive filter 40 (that is, n. m) is applied to a second input of the subtractor 42, where it is subtracted from the first signal $S_1$. The output of the subtractor 42 is denoted as $S_{out}$.

The output of the subtractor $S_{out}$ is used as an error signal to control the transfer function m of the adaptive filter 40.

Thus, from the discussion above:

$$S_{out}=(P+nT)-nm$$

The sounds P resulting from the wearer's heartbeat are relatively slowly changing, and so it is possible to adapt the transfer function m of the adaptive filter 40 more quickly than P varies.

Thus, it can be assumed that, during adaptation, P=0, and so, from the equation above:

$$S_{out}=nT-nm$$

The process of adaptation is performed so that the error signal $S_{out}$ becomes equal to zero, and so this equation becomes:

$$nT=nm$$

and therefore:

$$m=T$$

After the process of adaptation, as discussed above:

$$S_{out}=(P+nT)-nm$$

Because the adaptation has ensured that $$m=T$$

this in turn means that:

$$S_{out}=(P+nT)-nT$$

That is, $$S_{out}=P$$

Thus, the adaptation means that the effect of external noise is cancelled, and the output of the subtractor $S_{out}$ accurately represents the sounds P resulting from the wearer's heartbeat. This also removes any common mode noise between the two transducers 18, 22, for example cable noise in wired headsets.

Another issue that arises when detecting sounds to obtain a phonocardiogram in a person's ear canal is that sounds being produced by the loudspeaker in the earbud will interfere with the measurement.

Figure 4:
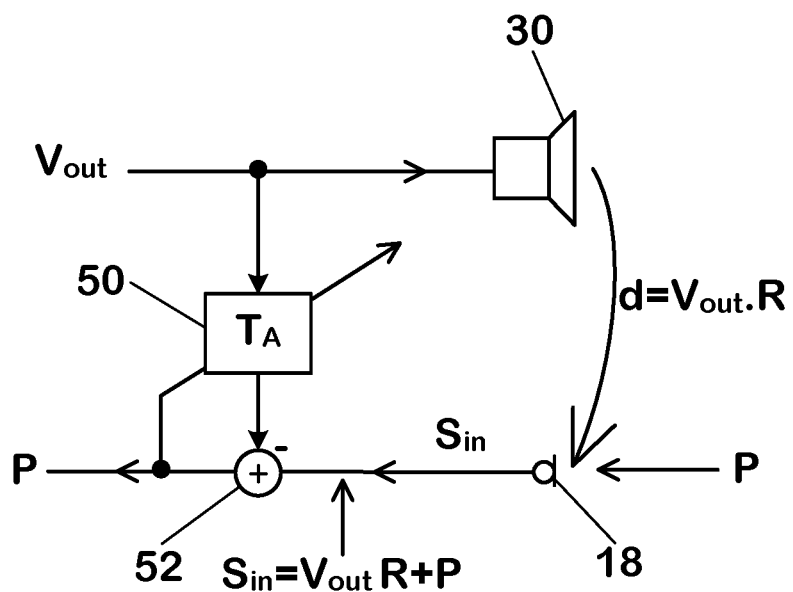
FIG. 4 illustrates a second form of signal processing applied to a signal obtained from a microphone in an earbud as shown in FIG. 1.

FIG. 4 illustrates a second form of signal processing applied to a signal obtained from a microphone in an earbud, in order to account for this.

FIG. 4 shows an embodiment based on FIGS. 1 and 2, in which a signal $V_{out}$ is applied to the loudspeaker 30 in order to generate sounds that the wearer of the earbud wants to hear, such as speech or music playback, or a telephone call.

The transducer 18 inside the ear canal detects not only the sounds P resulting from the wearer's heartbeat, but also a sound d that results from the output of the loudspeaker. The sound d is related to the loudspeaker input signal $V_{out}$ by a transfer function R that is associated with the loudspeaker transducer and the ear canal such that:

$$d = R \cdot V_{out}$$

The signal $S_{in}$ that is detected by the transducer 18 will therefore be a function of $(P + R \cdot V_{out})$.

In order to remove the effect of the sound d in the signal $S_{in}$, the loudspeaker input signal $V_{out}$ is applied to an adaptive filter 50, with the output of the adaptive filter 50 being subtracted in a subtractor 52 from the transducer output signal $S_{in}$. The transfer function R that is associated with the loudspeaker transducer and the ear canal is variable, and so the transfer function $T_A$ of the adaptive filter 50 is adapted as R varies such that the effect of the sound d is removed from the signal $S_{in}$, and hence the output signal of the subtractor 52 only represents the sounds P resulting from the wearer's heartbeat, assuming that the earphone is being worn at that time.

Returning to FIG. 2, the output signal generated by the audio transducer is passed to the heartbeat detection (HBD) block 34 for a determination to be made as to whether the output signal represents sounds that are characteristic of a person's heartbeat, and hence whether it can be determined that the earphone is being worn.

The heartbeat detection may be achieved by several means. Typically, the fact that a heart rate has a typical range of 60-120 bpm or 1-2 Hz is exploited.

For example, the heartbeat detection may be performed by peak detection of a band-limited signal.

As another example, the heartbeat detection may be performed by Kalman Filter tracking, for example using techniques described in connection with obtaining a heart rate measurement from an electrocardiogram signal in "Robust heart rate estimation from multiple asynchronous noisy sources using signal quality indices and a Kalman filter", Li, et al, Physiol Meas. 2008 January; 29(1): 15-32.

As another example, the heartbeat detection may be performed using a phase-locked loop locking to the peaks in the phonocardiogram.

As another example, the detected acoustic signal may be input into a Neural Network that has been trained using (a) inputs that represent heartbeats and (b) inputs that do not represent heartbeats, in order to distinguish whether the input acoustic signal does represent a heartbeat.

As another example, a system using an autocorrelation may be used for heartbeat detection.

Figure 5:
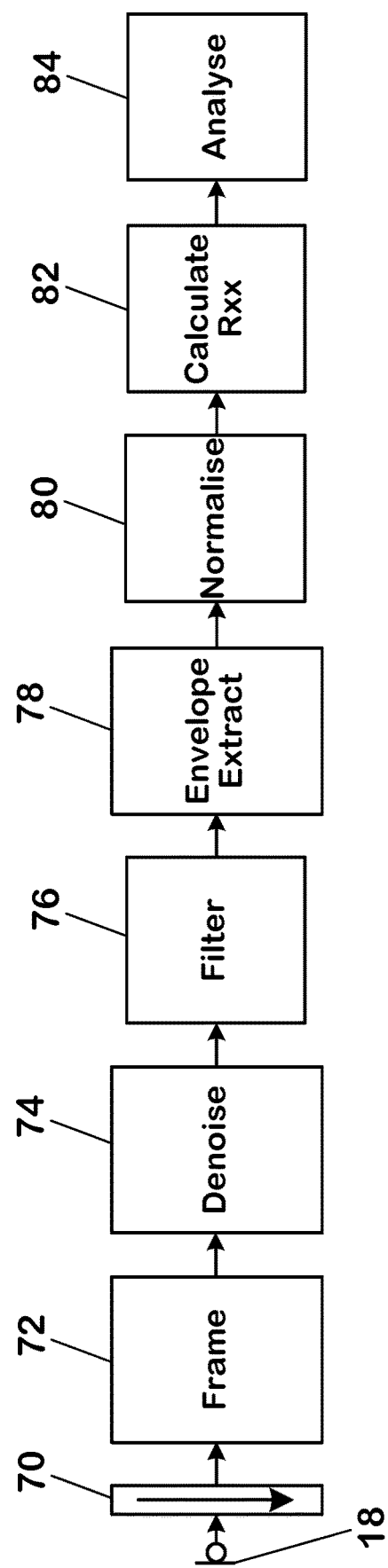
FIG. 5 illustrates a system for further processing of a signal obtained from a microphone in an earbud as shown in FIG. 1.

FIG. 5 is a block diagram, illustrating a system for heartbeat detection using autocorrelation to detect the presence of a signal component at a frequency that is typical of a heart rate. Any of the processing steps described herein may be performed by a suitably programmed processor, for example a digital signal processor (DSP) or a general purpose processor, for example in the earphone device, or in a host device to which the earphone is connected.

Thus, FIG. 5 shows a transducer, which is provided on an earphone, such that it is located in (acoustically coupled to) the ear of a person when they are wearing the earphone. As described above, the transducer may be an acoustic transducer 18, for example a microphone, a loudspeaker being used as a microphone, or an inertial measurement unit.

After any initial processing, for example as described with reference to FIG. 3 or FIG. 4 above, the input signal may be passed to an analog-digital converter. If this is a standard analog-digital converter, with a sample rate of, say, 192 kHz, then this sample rate is unnecessarily high, because the important information in a phonocardiogram has a bandwidth of around 500 Hz.

Therefore, this signal may be passed to a downsampler 70, which may for example downsample the acoustic signal to a sample rate of 1 kHz.

The downsampled signal may then be passed to a block 72 where it is split into frames. The length of a frame may for example be at least 1 s, and preferably long enough to include 2 cycles of the heartbeat, which may for example be 1.5-2 s.

The framed signal may then be denoised in block 74, for example using a wavelet.

The resulting signal may be passed to a filter 76, for example to remove spurious signal components that are not related to the heartbeat, originating for example from the movement (including the breathing) of the wearer. For example, the signal may be filtered with a high-pass filter having a cut-off frequency of (say) 20 Hz and/or may be filtered with a low-pass filter having a cut-off frequency of (say) 200 Hz. However, this filtering may not be necessary, because the spurious components may be ignored when the autocorrelation is generated.

In the embodiment shown in FIG. 5, the signal is then passed to an optional envelope extraction block 78. For example, this may simply take the absolute value of the signal, though using a Hilbert transform is also possible.

The resulting signal is passed to a normalisation block 80, where it is normalised, for example the mean is removed.

The normalised signal is passed to a block 82 where the autocorrelation Rxx is calculated. In this embodiment, it is only necessary to calculate the autocorrelation value for positive lags. The autocorrelation may then be normalised, for example such that Rxx(0)=1.

In the block 84, the autocorrelation is analysed, in order to determine whether the input audio signal contains components characteristic of a heartbeat.

Figure 6:
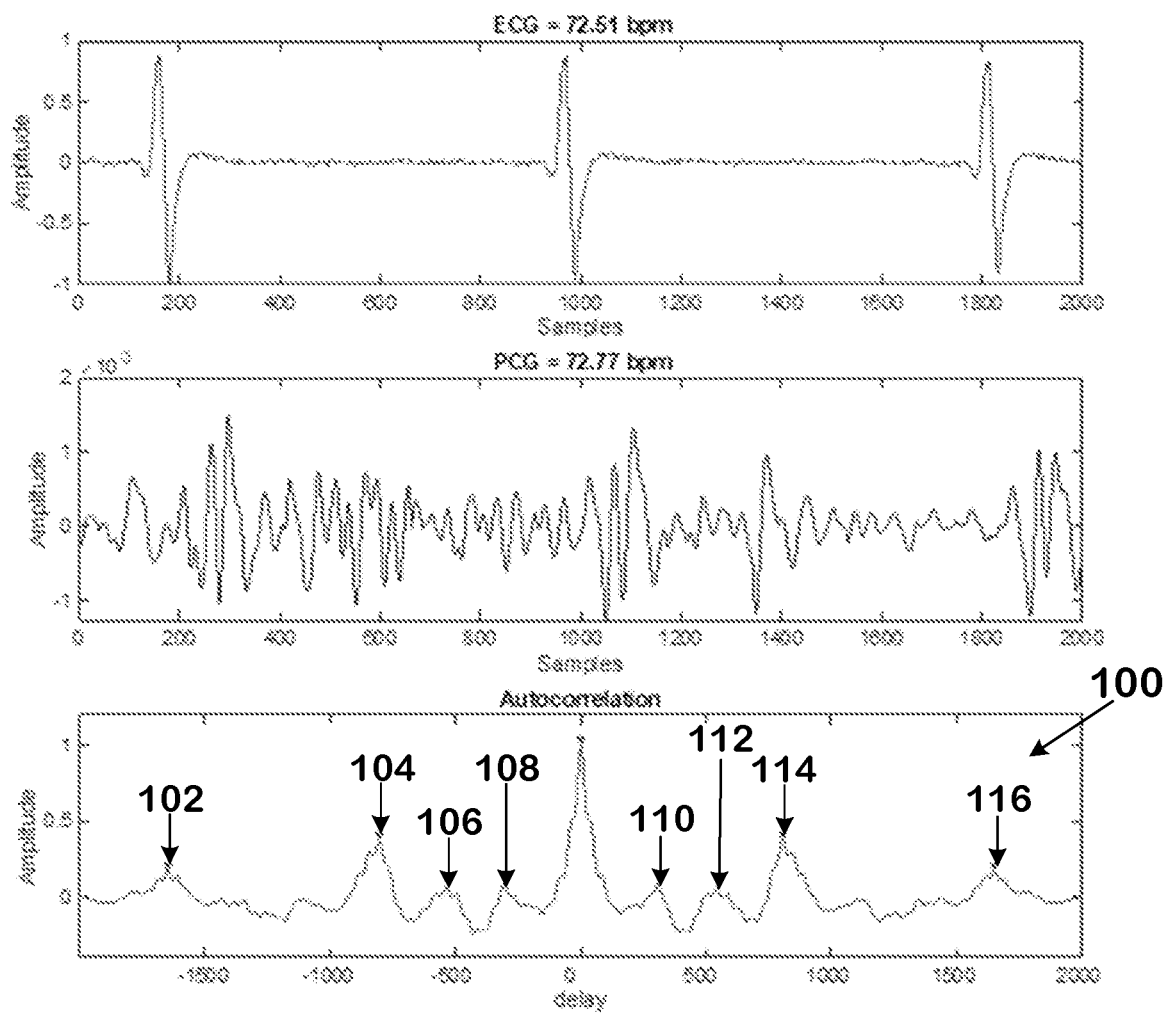
FIG. 6 illustrates a signal generated by the system of FIG. 5.

FIG. 6 shows the form of the autocorrelation function 100 that is generated by the block 82 in one example. FIG. 6 shows an electrocardiogram (ECG) signal for the purposes of comparison, and also shows the phonocardiogram (PCG). It will be noted that the phonocardiogram is a relatively noisy signal, from which it would be difficult to derive a heart rate value directly. However, FIG. 6 also shows the form of the autocorrelation function 100 that is generated by the block 82 from that PCG, and it can be seen that this contains clearer peaks that can be used for determining the heart rate. As mentioned above, the autocorrelation value only needs to be calculated for positive lags, and so the values shown for the negative lags in FIG. 6 are for illustrative purposes only.

In the autocorrelation function that is sent to the analysis block 84, the peaks 102, 104, 106, 108, 110, 112, 114, 116, shown in FIG. 6, are present. A minimum delay period dmin is set, corresponding to a very short period and hence to a frequency that is too high to be considered a likely heart rate. Thus, peaks in the autocorrelation that are too close to the delay=0 point are ignored.

In addition, a threshold amplitude of the peaks, for example equal to 0.1, is set, since peaks that are below this amplitude indicate a poor signal, and hence peaks in the autocorrelation that are below this amplitude are ignored.

In the example shown in FIG. 6, the peaks 102, 104, 106, 108 corresponding to negative lags are ignored. In addition, because they are within the minimum delay period dmin and/or below the threshold amplitude, the peaks 110, 112 are also ignored.

Thus, only the peaks 114, 116 are considered. These are spaced at integer multiples of 824 samples from the delay=0 point. With a sample rate of 1 kHz, a delay of 824 samples corresponds to a pulse period of 824 ms, and hence a heart rate of 72.77 bpm ($\cong$1.213 Hz).

If the earphone is not being worn, the calculated autocorrelation will probably not contain any peaks that correspond to any likely heart rate. Hence, when a calculated autocorrelation does not contain any significant peaks that correspond to any likely heart rate, it can be determined that the earphone is not being worn.

Thus, the autocorrelation can be used to identify signal components characteristic of a heartbeat, and hence can be used to determine that the sounds detected by the transducer include heartbeat sounds, and thus that the earphone is being worn.

Moreover, although one purpose of detecting the heartbeat in this example is to determine whether the earphone is being worn, it will be noted that the autocorrelation produces an accurate measurement for the heart rate of the person wearing the earphone. This can be supplied to any desired application for health-related use, for example for fitness tracking.

The embodiment above uses an autocorrelation technique to detect a heartbeat but, as a further alternative, there may be a two-stage approach, where the input signal is provided to a simple lossy neural network to make a quick initial determination of whether a heartbeat is present, while an autocorrelation is also performed as described above, in order to produce a potentially more accurate result, that requires data to be gathered over a longer time.

If a heartbeat is detected, using a transducer that is located within the ear canal of a person wearing the earphone, then it may be determined that the earphone is being worn by a user. By contrast, if no heartbeat is detected, it may be determined that the earphone is not being worn by a user.

In some embodiments, the process for detecting a heartbeat, as described above, may also be applied to a signal received from another transducer. For example, in the case of the earphone 12 shown in FIG. 1, the method may be applied to the signal received from the first transducer 18 that is located on or within a surface 20 of the earphone that extends into the ear canal 14 of the wearer, and may also be applied to the signal received from the second transducer 22 that is located on or within a surface 24 of the earphone that is exposed to the air 16. In some situations, the transducer that is located within the ear canal of a person wearing the earphone may appear to detect a heartbeat, but the second transducer may also appear to detect a heartbeat. The second transducer is not located in a position where it would be expected to detect sounds resulting from a heartbeat. Therefore, if both of these signals appear to detect a heartbeat, it can be assumed that this is for some spurious reason, and the detection made by the transducer that is located within the ear canal can be disregarded, and it can be assumed that the earphone is not being worn as intended.

Therefore, if no heartbeat is detected, or it is otherwise determined that the earphone is not being worn, the system may pause the playback of recorded sounds through the earphone. This allows the user to effectively pause playback of recorded sounds simply by removing the earphone, without needing to press a specific "pause" or "stop" button. If the absence of a heartbeat persists for a predetermined period of time, the system may power down a loudspeaker driver amplifier in order to save power.

The determination as to whether an earphone is being worn by a user may be used to detect a replay attack on a voice operated system. For example, in the case of a smartphone or other device operating on the basis of voice commands, in particular where speaker recognition is used to determine whether the commands have been spoken by an enrolled user of the system, one attack on such a system is to record the enrolled user's voice, and replay the recording to gain access to the system when the enrolled user is not present.

When such a voice command is detected by a microphone on an earphone (for example the microphone 22 in the earphone 12 shown in FIG. 1), a determination can be made as to whether the earphone is being worn by a user. If it is not being worn by a user, there is a possibility that the voice command detected by the microphone is not the voice of a live speaker, but is a recording.

As mentioned above, systems using voice as a biometric are in widespread use.

In a system as described with reference to the embodiments above, at least one sensor on an earphone is used to detect a heartbeat of a person wearing the earphone. According to further embodiments of the present disclosure, information can be obtained about properties of the detected heartbeat. This information about the properties of the detected heartbeat can then be used as a biometric identifier for the person wearing the earphone.

In certain embodiments, the sensor is an acoustic transducer, and more specifically might be a wide-band microphone that is able to generate signals across the useful bandwidth from about 20 Hz-500 Hz. In certain embodiments, a transducer that is able to produce low frequency signals with the required sensitivity (which might be a loudspeaker acting as a microphone as shown in FIG. 2) is used to detect whether the earphone is being worn, because the heartbeat detection only requires a bandwidth of a few Hz. If it is, then a transducer that is able to produce signals across a wider bandwidth may be activated. The transducer that is able to produce signals across a wider bandwidth may take the form of a loudspeaker acting as a microphone, in combination with a conventional microphone.

In certain embodiments, information about the timing properties of the detected heartbeat can be used as a biometric identifier for the person wearing the earphone.

As described above, an acoustic measurement of heart sounds is known as a phonocardiogram (PCG), which has a very different structure to the better-known electrocardiogram (ECG).

Figure 7:
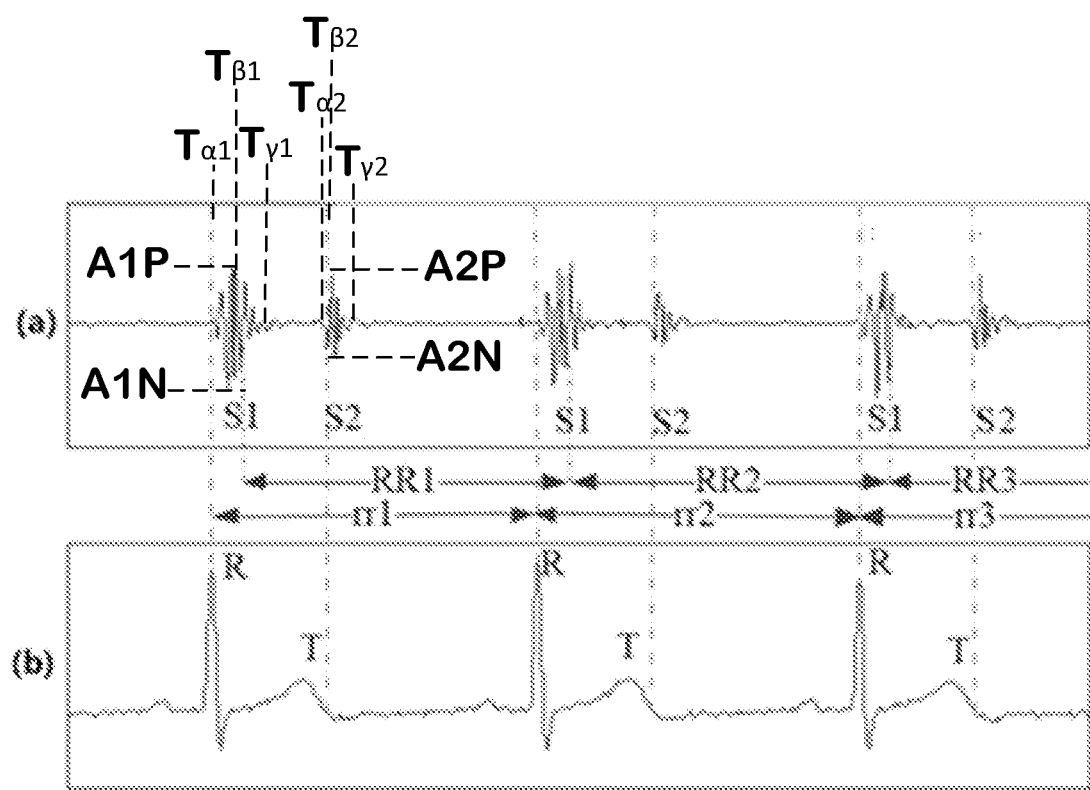
FIG. 7 illustrates a form of a phonocardiogram.

FIG. 7 illustrates a form of a phonocardiogram. Specifically, FIG. 7(a) shows the form of a phonocardiogram (PCG), and FIG. 7(b) shows the form of a corresponding electrocardiogram.

In a healthy heart, there are two key acoustic signatures, namely the first heart sound S1 corresponding to the systole, or contraction of the heart muscles, and the second heart sound S2 corresponding to the diastole, or relaxation of the heart muscles. These sounds represent the blood flow around the heart, but as mentioned above they can be measured in the ear canal.

Figure 8:
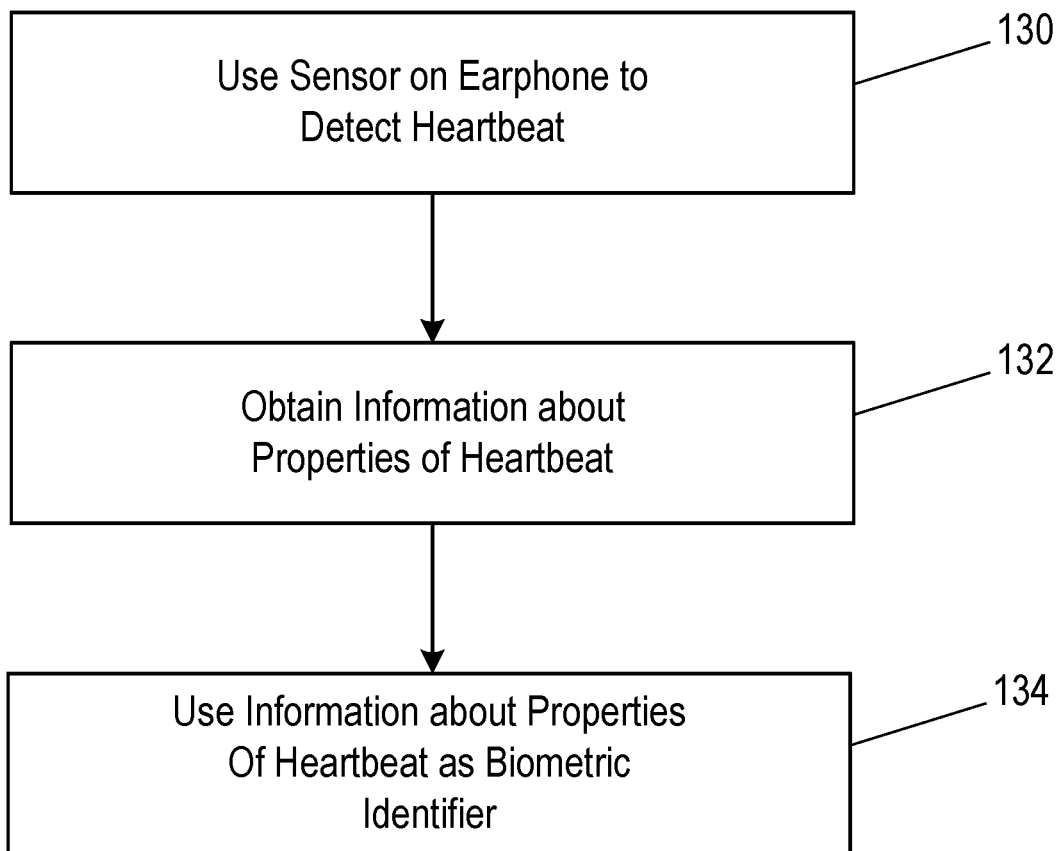
FIG. 8 is a flow chart illustrating a method in accordance with aspects of the disclosure.

FIG. 8 is a flow chart illustrating a method in accordance with this aspect of the disclosure. Any of the processing steps described herein may be performed by a suitably programmed processor, for example in the earphone device, or in a host device to which the earphone is connected.

Specifically, FIG. 8 shows a method of biometric authentication.

The method comprises, in step 130, using at least one sensor on an earpiece to detect a heartbeat of a person wearing the earpiece. As mentioned above, in certain embodiments, the sensor is an acoustic transducer, and more specifically might be a wide-band microphone that is able to generate signals across the useful bandwidth from about 20 Hz-500 Hz.

As described with reference to FIG. 2, a loudspeaker may be used as a microphone to detect low frequency signals. In order to detect signals across the useful bandwidth from 20 Hz-500 Hz, it may be necessary to detect signals using both a loudspeaker and another transducer, for example a conventional microphone, and to combine the signals generated by the two devices.

In one embodiment, a loudspeaker is used to detect acoustic signals. Because a heartbeat has a very low frequency, the loudspeaker is able to detect the signals that are necessary for the detection of the heartbeat, and hence for determining whether the earpiece is being worn by a user. In this one embodiment, this may be taken as a preliminary determination as to whether the earpiece is being worn.

If it is determined that the earpiece is being worn, then the second transducer can be activated, in order to generate signals at the higher frequencies. The resulting signal can then optionally be used in the more detailed on-ear detection method described with reference to FIG. 5.

When the second transducer has been activated, this allows the phonocardiogram waveform shown in FIG. 7(*a*) to be determined, and this allows the properties of the heartbeat to be studied in detail, as described below.

In step 132, the method comprises obtaining information about properties of the detected heartbeat.

In the case of an ECG, as shown in FIG. 7(*b*), the discriminative information is contained in the relative timing information between events. FIG. 7(*b*) shows the time intervals between successive R events as rr1, rr2, rr3, etc. The time difference between two events, for example the P event and the T event in any given cycle normalised relative to the period between successive R events, which can either be the period of the last cycle or can be averaged over a number of cycles.

In the case of a phonocardiogram, or PCG, as shown in FIG. 7(*a*), in general, there are two classes of information, namely time-based and amplitude-based. For both the S1 and S2 events there are onset (alpha), peak (beta) and end (gamma) events. FIG. 7(*a*) shows the time intervals between successive peaks in the S1 event as RR1, RR2, RR3, etc.

In the case of time-based information, the biometric information contained in the PCG is given by the relative timing of events in the PCG. For example, if the timings of the onset, peak, and end for the S1 event are designated Tα1, Tβ1 and Tγ1 respectively, and the onset, peak, and end for the S2 event are designated Tα2, Tβ2 and Tγ2 respectively, then useful biometric information can be contained in the value of the time between any pair of these timings, either relative to a time between another pair of these timings or relative to the duration of RR1, RR2, RR3, etc. The value of RR1, RR2, RR3 that is used can be the period in the current cycle or the average period over a number of cycles.

For example the duration of the S1 event (from Tα1 to Tγ1) as a fraction of the cycle period RR may provide useful biometric information. Alternatively, the duration of the S2 event (from Tα2 to Tγ2) as a fraction of the period between S2 events and S1 events (from Tγ2 to Tα1) may provide useful biometric information, just by way of example.

In the case of amplitude-based information, the positive and negative peak amplitudes of an S1 event can be designated as A1P and A1N respectively, while the positive and negative peak amplitudes of an S2 event can be designated as A2P and A2N respectively.

The amplitude-based biometric information contained in the PCG can then for example take the form of the ratio of any two such amplitude values, for example the ratio of A1P to A2N.

In practice, to improve performance several of these time-based and/or amplitude-based values can be fused to form a vector containing highly discriminative biometric information.

Thus, the step of obtaining information about properties of the detected heartbeat may comprise obtaining information about timing properties of the detected heartbeat and/or may comprise obtaining information about amplitude properties of the detected heartbeat.

The method of FIG. 8 then comprises step 134, namely using the information about the properties of the detected heartbeat as a biometric identifier.

Thus, in an enrolment phase, the selected biometric information is extracted while the known enrolling user is wearing the earphone, and stored in a database. For example, the metrics might be subjected to feature compression or reduction such as Linear Discriminative Analysis (LDA) before storage.

During a verification phase, the selected biometric information is extracted while a person is wearing the earphone, and the vector of the biometric information is compared with the information stored in the database for the enrolled user. Where the metrics are subjected to feature compression or reduction before storage in the enrolment phase, the same feature compression or reduction may be applied in the verification phase. A similarity test is then applied, to determine whether the person wearing the earphone is the enrolled user. For example, the distance between the stored metrics obtained during enrolment and the metrics obtained during verification may be calculated using cosine similarity.

There is thus described a system for detecting whether an earphone is being worn by a user, and a method of using information about the properties of a heartbeat, detected by a sensor on an earphone, as a biometric identifier.

Embodiments may be implemented as an integrated circuit which in some examples could be a codec or similar. Embodiments may be implemented in a host device, especially a portable and/or battery powered host device such as a mobile computing device for example a laptop, notebook or tablet computer, a games console, a remote control device, a home automation controller or a domestic appliance including a domestic temperature or lighting control system, a toy, a machine such as a robot, an audio player, a video player, or a mobile telephone for example a smartphone. The device could be a wearable device such as a smartwatch. It will be understood that embodiments may be implemented as part of a system provided in a home appliance or in a vehicle or interactive display. The amplifier circuit may be an audio amplifier used to drive an audio transducer such as a loudspeaker or surface audio system, but it will be understood that the amplifier may be used to drive other transducers, e.g. a vibrational transducer such as a linear resonant actuator for the generation of haptic effects. There is further provided a host device incorporating the above-described system.

The skilled person will recognise that some aspects of the above-described apparatus and methods, for example the discovery and configuration methods may be embodied as processor control code, for example on a non-volatile carrier medium such as a disk, CD- or DVD-ROM, programmed memory such as read only memory (Firmware), or on a data carrier such as an optical or electrical signal carrier. For many applications, embodiments will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog™ or VHDL (Very high speed integrated circuit Hardware Description Language). As the skilled person will appreciate, the code may be distributed between a plurality of coupled components in communication with one another. Where appropriate, the embodiments may also be implemented using code running on a field-(re) programmable analogue array or similar device in order to configure analogue hardware.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. A method of detecting whether an earpiece is being worn by a user, the method comprising:
using at least one sensor on the earpiece to detect a heartbeat; and
if a heartbeat is detected, determining that the earpiece is being worn by a user, wherein using at least one sensor on the earpiece to detect a heartbeat comprises:
receiving a signal from the at least one sensor;
obtaining samples of the received signal;
calculating an autocorrelation using the samples of the received signal; and
detecting the heartbeat from at least one peak in the calculated autocorrelation.

2. A method according to claim 1, further comprising:
if no heartbeat is detected, determining that the earpiece is not being worn by a user; and
determining that a speech signal detected by a microphone on the earpiece may not come from a live speaker.

3. A method according to claim 1, further comprising:
if no heartbeat is detected, determining that the earpiece is not being worn by a user; and
powering down an output amplifier connected to a loudspeaker of the earpiece or suspending playback of audio signals through the earpiece.

4. A method according to claim 1, wherein using at least one sensor on the earpiece to detect a heartbeat comprises:
using an accelerometer on the earpiece to detect vibrations indicative of a heartbeat.

5. A method according to claim 1, wherein using at least one sensor on the earpiece to detect a heartbeat comprises: detecting electrical signals associated with a heartbeat.

6. A method according to claim 1, wherein using at least one sensor on the earpiece to detect a heartbeat comprises: using an inertial measurement unit configured to detect movement in an ear canal of the user if the earpiece is being worn by the user.

7. A method according to claim 1, wherein using at least one sensor on the earpiece to detect a heartbeat comprises: using at least one audio transducer to obtain a signal representing sound in the vicinity of the earpiece.

8. A method according to claim 7, wherein the at least one audio transducer comprises a loudspeaker on the earpiece.

9. A method according to claim 7, further comprising: applying said signal representing sound in the vicinity of the earpiece to an analog-digital converter, wherein the analog-digital converter is switched on only when detecting whether the earpiece is being worn by a user.

10. A method according to claim 7, comprising:
using a first audio transducer to generate a first audio signal, wherein the first audio transducer is positioned on the earpiece so as to detect sounds in an ear canal of a user, when the earpiece is being worn normally;
using a second audio transducer to generate a second audio signal, wherein the second audio transducer is positioned on the earpiece so as to detect sounds outside an ear of a user, when the earpiece is being worn normally;
applying the second audio signal to an adaptive filter to generate a filtered second audio signal, wherein the adaptive filter is configured to represent a transfer function experienced by sound travelling from outside the ear of a user to inside the ear canal of the user; and
subtracting the filtered second audio signal from the first audio signal to generate said signal representing sound in the vicinity of the earpiece.

11. A method according to claim 7, further comprising:
applying the signal representing sound in the vicinity of the earpiece to a first input of a subtractor;
applying a signal to be applied to a loudspeaker in the earpiece to an adaptive filter to generate a filtered signal; and
applying the filtered signal to a second input of the subtractor,
wherein the adaptive filter is adapted to reproduce an effect of applying the signal to the loudspeaker and detecting the resulting sound using said at least one audio transducer, such that an effect of the signal to be applied to the loudspeaker is minimised in an output of the subtractor.

12. A method according to claim 1, wherein using at least one sensor on the earpiece to detect a heartbeat comprises:
receiving a signal from the sensor;
obtaining samples of the received signal;
calculating an autocorrelation using the samples of the received signal;
detecting the heartbeat from at least one peak in the calculated autocorrelation.

13. A method according to claim 12, comprising obtaining said samples of the received signal at a sample rate below 1 kHz.

14. A method according to claim 13, comprising receiving the signal in digital form with a sample rate higher than 1 kHz, and downsampling the received signal to a sample rate below 1 kHz.

15. A method according to claim 12, wherein detecting the heartbeat from at least one peak in the calculated autocorrelation comprises:
ignoring peaks that correspond to frequencies below a range of likely human heart rates; and
ignoring peaks having a height below a threshold height.

16. A method according to claim 1, wherein using at least one sensor on the earpiece to detect a heartbeat comprises:
receiving a signal from the sensor; and
determining whether said signal contains a component at a frequency consistent with a heartbeat, for example in the region of 0.75 Hz 3 Hz.

17. A method according to claim 16, wherein determining whether said signal contains a component at a frequency consistent with a heartbeat comprises:
band-pass filtering the signal to pass components of the signal in a frequency range consistent with a heartbeat, and
detecting a peak component of the band-pass filtered signal.

18. A method according to claim 16, wherein determining whether said signal contains a component at a frequency consistent with a heartbeat comprises:
applying said signal to a phase locked loop, and determining a frequency at which the loop is locked.

19. A method according to claim 1, comprising:
using at least one first sensor on the earpiece to detect a heartbeat; and
if a heartbeat is detected, making a preliminary determination that the earpiece is being worn by a user, and activating at least one second sensor on the earpiece;
using the at least one second sensor on the earpiece to detect a heartbeat; and
if a heartbeat is detected, determining that the earpiece is being worn by a user.

20. A method according to claim 1, comprising:
receiving a first signal from at least one first sensor on the earpiece, wherein the at least one first sensor is positioned on the earpiece such that it is able to detect a heartbeat, when the earpiece is being worn in an expected way;
determining whether the first signal comprises features characteristic of a heartbeat;
receiving a second signal from at least one second sensor on the earpiece, wherein the at least one second sensor is positioned on the earpiece such that it is not able to detect a heartbeat, when the earpiece is being worn in the expected way;
determining whether the second signal comprises features characteristic of a heartbeat;
and
if it is determined that the first signal comprises features characteristic of a heartbeat and that the second signal comprises features characteristic of a heartbeat, determining that the earpiece is not being worn in the expected way; or
if it is determined that the first signal comprises features characteristic of a heartbeat and that the second signal does not comprise features characteristic of a heartbeat, determining that the earpiece is being worn in the expected way.

21. A system comprising a processor, wherein the processor is configured for performing a method according to claim 1.

22. A computer program product, comprising a tangible and/or non-volatile computer readable medium, comprising computer readable instructions for causing a processor to perform a method according to claim 1.

23. A method of detecting whether an earpiece is being worn by a user, the method comprising:
   using at least one sensor on the earpiece to detect a heartbeat; and
   if a heartbeat is detected, determining that the earpiece is being worn by the user,
   wherein using the at least one sensor on the earpiece to detect the heartbeat comprises:
   using at least one audio transducer to obtain a signal representing sound in the vicinity of the earpiece; and
   applying said signal representing sound in the vicinity of the earpiece to an analog-digital converter, wherein the analog-digital converter is switched on only when detecting whether the earpiece is being worn by the user.

24. A method of detecting whether an earpiece is being worn by a user, the method comprising:
   using at least one sensor on the earpiece to detect a heartbeat; and
   if a heartbeat is detected, determining that the earpiece is being worn by the user,
   wherein using the at least one sensor on the earpiece to detect the heartbeat comprises:
   using a first audio transducer to generate a first audio signal, wherein the first audio transducer is positioned on the earpiece so as to detect sounds in an ear canal of a user, when the earpiece is being worn normally;
   using a second audio transducer to generate a second audio signal, wherein the second audio transducer is positioned on the earpiece so as to detect sounds outside an ear of a user, when the earpiece is being worn normally;
   applying the second audio signal to an adaptive filter to generate a filtered second audio signal, wherein the adaptive filter is configured to represent a transfer function experienced by sound travelling from outside the ear of a user to inside the ear canal of the user; and
   subtracting the filtered second audio signal from the first audio signal to generate a signal representing sound in the vicinity of the earpiece.

25. A method of detecting whether an earpiece is being worn by a user, the method comprising:
   using at least one sensor on the earpiece to detect a heartbeat; and
   if a heartbeat is detected, determining that the earpiece is being worn by the user,
   wherein using the at least one sensor on the earpiece to detect the heartbeat comprises:
   using at least one audio transducer to obtain a signal representing sound in the vicinity of the earpiece;
   applying the signal representing sound in the vicinity of the earpiece to a first input of a subtractor;
   applying a signal to be applied to a loudspeaker in the earpiece to an adaptive filter to generate a filtered signal; and
   applying the filtered signal to a second input of the subtractor,
   wherein the adaptive filter is adapted to reproduce an effect of applying the signal to the loudspeaker and detecting the resulting sound using said at least one audio transducer, such that an effect of the signal to be applied to the loudspeaker is minimised in an output of the subtractor.

26. A method of detecting whether an earpiece is being worn by a user, the method comprising:
   using at least one sensor on the earpiece to detect a heartbeat; and
   if a heartbeat is detected, determining that the earpiece is being worn by the user,
   wherein using at least one sensor on the earpiece to detect a heartbeat comprises:
   receiving a signal from the sensor; and
   determining whether said signal contains a component at a frequency consistent with a heartbeat by applying said signal to a phase locked loop, and determining a frequency at which the loop is locked.

27. A method of detecting whether an earpiece is being worn by a user, the method comprising:
   using at least one first sensor on the earpiece to detect a heartbeat; and
   if a heartbeat is detected using the first sensor, making a preliminary determination that the earpiece is being worn by a user, and activating at least one second sensor on the earpiece; using the at least one second sensor on the earpiece to detect a heartbeat; and
   if a heartbeat is detected using the second sensor, determining that the earpiece is being worn by the user.

28. A method of detecting whether an earpiece is being worn by a user, the method comprising:
   receiving a first signal from at least one first sensor on the earpiece, wherein the at least one first sensor is positioned on the earpiece such that it is able to detect a heartbeat, when the earpiece is being worn in an expected way;
   determining whether the first signal comprises features characteristic of a heartbeat;
   receiving a second signal from at least one second sensor on the earpiece, wherein the at least one second sensor is positioned on the earpiece such that it is not able to detect a heartbeat, when the earpiece is being worn in the expected way;
   determining whether the second signal comprises features characteristic of a heartbeat; and
   if it is determined that the first signal comprises features characteristic of a heartbeat and that the second signal comprises features characteristic of a heartbeat, determining that the earpiece is not being worn in the expected way; or
   if it is determined that the first signal comprises features characteristic of a heartbeat and that the second signal does not comprise features characteristic of a heartbeat, determining that the earpiece is being worn in the expected way.

* * * * *

UNITED STATES PATENT AND TRADEMARK OFFICE
CERTIFICATE OF CORRECTION

| | |
|---|---|
| PATENT NO. | : 11,534,100 B2 |
| APPLICATION NO. | : 17/094867 |
| DATED | : December 27, 2022 |
| INVENTOR(S) | : John P. Lesso |

It is certified that error appears in the above-identified patent and that said Letters Patent is hereby corrected as shown below:

In the Claims

In Column 18, Line 12, in Claim 16, delete "0.75 Hz 3 Hz" and insert -- 0.75 Hz-3 Hz. --, therefor.

Signed and Sealed this
Ninth Day of May, 2023

Katherine Kelly Vidal
*Director of the United States Patent and Trademark Office*